US011413215B2

(12) United States Patent
Shaw et al.

(10) Patent No.: US 11,413,215 B2
(45) Date of Patent: Aug. 16, 2022

(54) METHODS FOR EVALUATING EFFECTIVENESS OF RESUSCITATION EFFORTS DURING A CARDIAC CRISIS

(71) Applicants: Sense Diagnostics, Inc., Cincinnati, OH (US); University Of Cincinnati, Cincinnati, OH (US)

(72) Inventors: George Jerome Shaw, Cincinnati, OH (US); Joseph Korfhagen, Blue Ash, OH (US)

(73) Assignees: Sense Diagnostics, Inc., Cincinnati, OH (US); University of Cincinnati, Cincinnati, OH (US)

(*) Notice: Subject to any disclaimer, the term of this patent is extended or adjusted under 35 U.S.C. 154(b) by 919 days.

(21) Appl. No.: 16/167,944

(22) Filed: Oct. 23, 2018

(65) Prior Publication Data
US 2019/0117500 A1 Apr. 25, 2019

Related U.S. Application Data

(60) Provisional application No. 62/575,664, filed on Oct. 23, 2017.

(51) Int. Cl.
*A61B 5/05* (2021.01)
*A61H 31/00* (2006.01)
(Continued)

(52) U.S. Cl.
CPC .......... *A61H 31/005* (2013.01); *A61B 5/0042* (2013.01); *A61B 5/0265* (2013.01);
(Continued)

(58) Field of Classification Search
CPC .............. A61H 31/005; A61H 2230/65; A61B 5/0042; A61B 5/0265; A61B 5/05;
(Continued)

(56) References Cited

U.S. PATENT DOCUMENTS

2016/0007879 A1 1/2016 Gonzalez et al.
2016/0278653 A1* 9/2016 Clark ................ A61B 5/746
(Continued)

OTHER PUBLICATIONS

European Patent Office, International Searching Authority, International Search Report issued in corresponding PCT Application No. PCT/US2018/057033, dated Feb. 5, 2019 (7 pages).
(Continued)

*Primary Examiner* — Rex R Holmes
(74) *Attorney, Agent, or Firm* — Wood Herron & Evans LLP

(57) ABSTRACT

Described are a device and method for detecting cerebral perfusion in a subject's head during a cardiac crisis. Embodiments of the device include a neurological status evaluation apparatus having a signal generator configured to generate an electromagnetic signal at one or more frequencies, a transmitting antenna coupled to the signal generator and configured to transmit the electromagnetic signal, and a receiving antenna positioned proximate to the transmitting antenna such that an evaluation space is defined between the transmitting antenna and the receiving antenna. In embodiments, the subject's head does not contact the transmitting antenna or the receiving antenna. The receiving antenna receives a modulated electromagnetic signal after propagating through the subject's head. The neurological status evaluation apparatus further includes a signal analyzer coupled to the receiving antenna, wherein the signal analyzer receives and samples the modulated electromagnetic signal. A computing device is coupled to the signal analyzer, calculates an evaluation, and provides a neurological status indicator of the subject's head based on the evaluation parameter.

11 Claims, 6 Drawing Sheets

(51) Int. Cl.
  *A61B 5/00*    (2006.01)
  *A61B 5/0265*   (2006.01)
  *H01Q 9/04*    (2006.01)
  *H01Q 1/24*    (2006.01)
  *H01Q 1/27*    (2006.01)

(52) U.S. Cl.
  CPC .............. *A61B 5/05* (2013.01); *A61B 5/4836* (2013.01); *A61B 5/4848* (2013.01); *A61B 5/7228* (2013.01); *A61H 2230/65* (2013.01); *H01Q 1/24* (2013.01); *H01Q 1/27* (2013.01); *H01Q 9/0464* (2013.01)

(58) Field of Classification Search
  CPC ... A61B 5/4836; A61B 5/4848; A61B 5/7228; H01Q 1/24; H01Q 1/27; H01Q 9/0464
  See application file for complete search history.

(56) References Cited

U.S. PATENT DOCUMENTS

| | | |
|---|---|---|
| 2017/0055839 A1 | 3/2017 | Levinson et al. |
| 2017/0127946 A1* | 5/2017 | Levinson ............. A61B 5/0042 |
| 2017/0231524 A1 | 8/2017 | Rubinsky et al. |

OTHER PUBLICATIONS

European Patent Office, International Searching Authority, Written Opinion issued in corresponding PCT Application No. PCT/US2018/057033, dated Feb. 5, 2019 (6 pages).

\* cited by examiner

METHODS FOR EVALUATING EFFECTIVENESS OF RESUSCITATION EFFORTS DURING A CARDIAC CRISIS

RELATED APPLICATIONS

This application is a non-provisional application claiming priority to U.S. Provisional Patent Application No. 62/575,664 filed on Oct. 23, 2017, the disclosure of which is hereby incorporated by reference herein in its entirety, This invention was made with U.S. Government support under NSF #IIP-1520285 awarded by the National Science Foundation. The U.S. Government has certain rights in this invention.

BACKGROUND

Cardiac arrest is a devastating medical event with little chance of return of spontaneous circulation (ROSC) in most adults. During cardiac arrest, blood flow to the brain is interrupted. This results in anoxia at the microscopic level. Neurons are the most metabolically active cells in the human body, and most of the energy is consumed by the Na—K pumps that maintain the electrical gradient across the cell membranes. Without these gradients, the cell is unable to maintain nerve conduction and the generation of neuronal axon potentials. Conversely, if the neuron is adequately perfused, the Na—K pumps have sufficient energy to maintain these gradients.

The odds for a good neurologic outcome are even worse. In 2016, the incidence of out of hospital cardiac arrest was over 350,000 with a survival to hospital discharge rate of 12%. In addition, less than 10% of cardiac arrest patients have a good neurologic outcome. After several minutes of 'no flow' to the brain, irreversible brain damage can occur.

The main initial treatment for a person in cardiac arrest is cardiopulmonary resuscitation ("CPR"). CPR causes a 'low flow' state to the brain and other vital organs such that upon ROSC, damage is minimized, particularly to the brain. The effectiveness of CPR for providing blood flow to the brain may be dependent on the training of the person administering CPR as well as on the physical condition of the patient. Currently, there are no non-invasive devices for monitoring brain function during CPR to ensure adequacy of brain function upon ROSC.

Accordingly, a need exists for non-invasive neurologic monitoring of brain function during resuscitation efforts for a patient in the midst of a cardiac crisis, such as a patient in cardiac arrest, that does not require a trained technician, and may be deployed in a wide variety of settings, such as emergency rooms, first responder vehicles, health care facilities, nursing care facilities, and the like.

SUMMARY

In an embodiment, a neurological status evaluation apparatus includes a signal generator configured to generate an electromagnetic signal at one or more frequencies, a transmitting antenna coupled to the signal generator, wherein the transmitting antenna is configured to transmit the electromagnetic signal, and a receiving antenna positioned proximate to the transmitting antenna such that an evaluation space is defined between the transmitting antenna and the receiving antenna. The evaluation space is configured to receive the head of a subject such that the subject's head does not contact the transmitting antenna nor the receiving antenna. The receiving antenna receives a modulated electromagnetic signal after propagating through the subject's head. The neurological status evaluation apparatus further includes a signal analyzer coupled to the receiving antenna, wherein the signal analyzer receives the modulated electromagnetic signal and samples spectrum data of the modulated electromagnetic signal, and a computing device coupled to the signal analyzer. The computing device calculates an evaluation parameter based at least in part on the sampled spectrum data of the modulated electromagnetic signal, and provides a neurological status indicator for the subject based at least in part on the evaluation parameter. In an embodiment, the neurological status indicator indicates the sufficiency of blood flow to the subject's brain during resuscitation efforts, such as during CPR.

In another embodiment, a transcranial neurological evaluation apparatus includes a signal configured to generate an electromagnetic signal at one more frequencies, a headband portion configured to be positioned about a human subject's head, and a plurality of transceiver devices positioned on the headband portion. Each individual transceiver device of the plurality of transceiver devices includes a transmitting antenna coupled to the signal generator, and a receiving antenna. The transmitting antenna is configured to transmit the electromagnetic signal. The transmitting antenna and the receiving antenna do not make electrical contact with the subject's head, and the receiving antenna receives a modulated electromagnetic signal after propagating through a brain of the subject's head. The transcranial neurological evaluation apparatus further includes a signal analyzer coupled to the receiving antenna of each transceiver device of the plurality of transceiver devices, and a computing device coupled to the signal analyzer. The signal analyzer receives the modulated electromagnetic signal and samples spectrum data of the modulated electromagnetic signal. The computing device calculates an evaluation parameter for each transceiver device based at least in part on the sampled spectrum data of each modulated electromagnetic signal, and provides a neurological status indicator of the brain based at least in part on one or more of the evaluation parameters.

In yet another embodiment, a method of evaluating the neurological status of a subject during a cardiac crisis, the method includes transmitting an electromagnetic signal into the subject's head, and receiving a modulated electromagnetic signal from the subject's head, wherein the electromagnetic signal is transmitted from a transmitting antenna that is not in electrical contact with the subject's head, and the modulated electromagnetic signal is received by a receiving antenna that is not in electrical contact with the subject's head. The method further includes sampling spectrum data of the modulated electromagnetic signal, and calculating an evaluation parameter based at least in part on the sampled spectrum data of the modulated electromagnetic signal, wherein the evaluation parameter corresponds to a dielectric or conductive property of the biological tissue under evaluation. The method additionally includes providing a neurological status indicator of the subject's brain based at least in part on the evaluation parameter. In an embodiment, the neurological status indicator provides information to a person administering a resuscitation effort to a subject regarding the effectiveness of the resuscitation efforts. An exemplary cardiac crisis is cardiac arrest and an exemplary resuscitation effort is cardiopulmonary resuscitation (CPR).

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
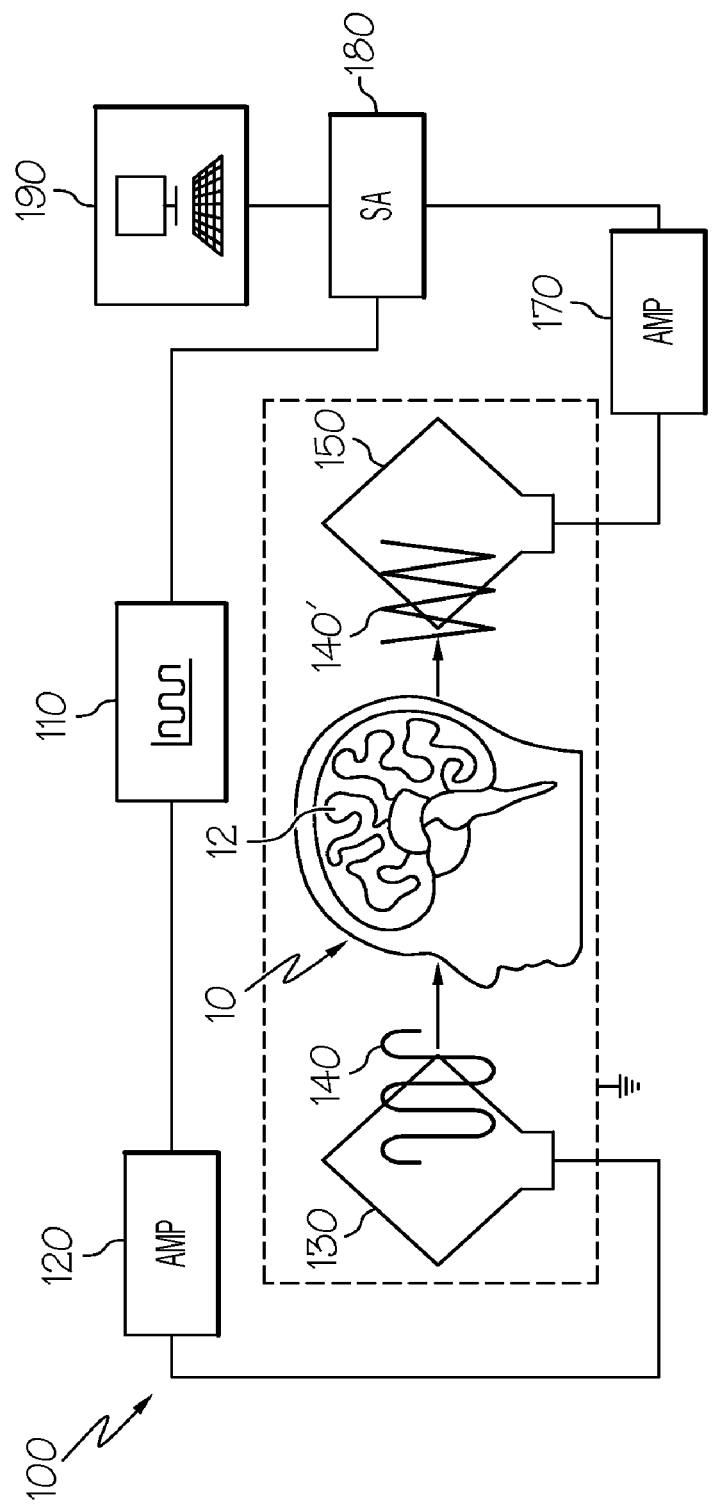
FIG. 1 depicts a schematic illustration of a neurological evaluation apparatus according to one or more embodiments shown and described herein.

Embodiments of the present disclosure are directed to apparatuses and methods for detecting and evaluating the neurological status of a subject's brain during a cardiac crisis, such as during cardiac arrest. The embodiments described herein provide an indicator of changes in neurologic function of the subject's brain during resuscitation efforts, such as during CPR. Generally, embodiments subject the subject's head, and more particularly, the subject's brain, to a non-invasive, tailored electromagnetic signal. The electromagnetic signal is input into the subject's head by a transmitting antenna, wherein it then interacts with the subject's brain. The resulting modulated electromagnetic signal that is modulated by the subject's head, and in particular, the subject's brain, is then received by a receiving antenna. The electromagnetic signal transmitted by the transmitting antenna may be altered by the electrical properties of the subject's brain (e.g., resistance, conductance, and dielectric properties), and the altered/modulated electromagnetic signal having passed through the subject's brain is received by the receiving antenna. Modulation of the electromagnetic signal within the subject's brain can be caused by (1) alterations in the electrical properties of the central nervous system, such as the permittivity $\varepsilon$ or conductivity $\sigma$, and (2) by changes in blood flow in the central nervous system. Embodiments utilize different frequencies of electromagnetic radiation to allow detection of the neurological status of the subject during the cardiac crisis. Embodiments detect the neurological status of the subject to evaluate the effectiveness of resuscitation efforts, such the effectiveness of CPR. It is noted that although embodiments of the present disclosure are described in the context of cardiac arrest and CPR, embodiments are not limited thereto. A decrease in cerebral perfusion below a threshold necessary to maintain neuronal cell electrical gradients will result in a change in $\varepsilon$ and $\sigma$. Such changes in $\varepsilon$ and $\sigma$ will result in substantial changes to the RF signal input by the device.

In an embodiment, an electromagnetic signal from an antenna is passed through the head of a subject in the midst of a cardiac crisis. The subject may be receiving a resuscitation effort, such as CPR. After passing through the subject's head, the electromagnetic signal is received by an antenna. The received electromagnetic signal is evaluated and may result in an alarm to alert the treating responder that the resuscitation efforts are not providing sufficient blood flow to the brain of the subject and that further resuscitation efforts may be required. If CPR is adequate to maintain cell perfusion, the change of the evaluation parameter based on the RF signal ($\theta$) will be small and below the threshold change from normal. If $\theta$ is large, CPR is not adequate and the caregiver will be prompted to take measures to improve blood flow.

Embodiments of the device may be useful to predict neurological outcome for a patient experiencing a cardiac crisis. In an embodiment, a threshold parameter based on the RF signal $\theta_T$ is established. If the $\theta$ is larger than the $\theta_T$ for a specified duration of time, then the patient is predicted to have a poor neurologic outcome and resuscitation efforts can be discontinued. If $\theta$ does not exceed $\theta_T$, then the patient is predicted to have a better neurologic outcome, and resuscitative efforts should continue. In an embodiment, the specified duration is at least 10 minutes, and in another embodiment, the specified duration is 30 minutes.

In embodiments of the invention, the threshold RF signal $\theta_T$ is based on historical data of RF signals from subjects with cerebral blood flow sufficient to maintain electrical gradients and have a good neurologic outcome and RF signals from subjects with insufficient cerebral blood flow to maintain electrical gradients who suffer a poor neurologic outcome. In another embodiment, the threshold RF signal $\theta_T$ may be a percentage decrease of an average signal value from a population of subjects having sufficient cerebral blood flow to maintain electrical gradients. For example, in an embodiment, the threshold RF signal $\theta_T$ may be at least 10% less than the signal from a population of subjects with sufficient cerebral blood flow and in another embodiment, the threshold RF signal $\theta_T$ may be at least 20% less than the signal from a population of subjects with sufficient cerebral blood flow, and in yet another embodiment, the threshold RF signal $\theta_T$ may be at least 30% less than the signal from a population of subjects with sufficient cerebral blood flow.

Embodiments of the invention may be useful in first responder settings, including, but not limited to, first aid stations, first responder kits, ambulances, firetrucks, police cars, automatic external defibrillators (AEDs) and emergency rooms. Embodiments of the invention may also be useful in critical care monitoring settings including, but not limited to, the intensive care unit (ICU) or neurosurgical intensive care unit (NICU) of hospitals.

Accordingly, embodiments of the present disclosure are directed to non-invasive, field deployable, continuous brain monitors that detect ongoing neuronal activity during a cardiac event and that may relate to the sufficiency of blood flow to the subject's brain during resuscitation efforts, such as during CPR.

Referring now to FIG. 1, a schematic illustration of a neurological status evaluation apparatus 100 to evaluate a subject's brain 12 according to an embodiment is provided. The neurological status evaluation apparatus depicted in FIG. 1 is configured to detect neurological status of a subject's brain during a cardiac crisis. The neurological status evaluation apparatus 100 generally comprises a signal generator 110, a first amplifier 120, a transmitting antenna 130, a receiving antenna 150, a second amplifier 170, a signal analyzer 180, and a computing device 190.

The signal generator 110 may be configured as any signal generator device or circuit capable of generating the desired electromagnetic signal 140 at the desired frequency and amplitude. The properties of the electromagnetic signal 140 are described in more detail below, and may depend on the particular application in which the neurological status evaluation apparatus is to be utilized. In an embodiment, the signal generator 110 is capable of producing an electromagnetic signal at a frequency within the range of about 0.9 GHz to about 3 GHz. The first amplifier 120 is provided to amplify the signal produced by the signal generator 110 to a desired power level. The first amplifier 120 may be included in the signal generator 110 as a single component, in some embodiments.

The transmitting antenna 130 is electrically coupled to either the first amplifier 120 or the signal generator 110 such that it receives the electromagnetic signal 140 for transmission toward and through the subject's brain 12. In an embodiment, the transmitting antenna 130 is a directional antenna that is configured to directionally propagate the electromagnetic signal 140 toward the subject's brain 12.

The transmitting antenna 130 and the receiving antenna 150 are arranged to define an evaluation space for the subject's head, including the subject's brain 12. Unlike conventional devices that provide for passive measurements of the signals produced by the brain, the transmitting antenna 130 and the receiving antenna 150 are arranged such that transmitting antenna 130 and the receiving antenna 150 are not in electrical contact with the subject's head that is positioned within the evaluation space. This allows for free propagation of the electromagnetic signal 140 through the subject's brain 12.

As shown in FIG. 1 and described in more detail below, the electromagnetic signal 140 enters the subject's brain 12 where it is modulated by the brain's dielectric properties such that a modulated electromagnetic signal 140' is received by the receiving antenna 150. The receiving antenna 150 may be electrically coupled to the second amplifier 170 such that the modulated electromagnetic signal 140' is passed to the second amplifier 170 for amplification. The amplified electromagnetic signal is then provided to a signal analyzer 180. It should be understood that in some embodiments, the modulated electromagnetic signal 140' may be provided directly to the signal analyzer 180 without additional amplification by the second amplifier 170.

The signal analyzer 180 is configured to sample the spectrum data of the modulated electromagnetic signal over a desired frequency range. The signal analyzer 180 may be configured as any device or circuit capable of sampling the spectrum data of the electromagnetic signal. As an example and not a limitation, the signal analyzer 180 includes an HP 8560E signal analyzer manufactured by Hewlett-Packard. Any signal analyzer may be used.

The signal analyzer 180 may be communicatively coupled to a computing device 190, which may take on a wide variety of configurations. The computing device 190 may include, but is not limited to, a general-purpose computer, a special-purpose computer, a laptop computer, a tablet computer, a mobile device, or a proprietary microcontroller circuit. In one embodiment, the functionality of the signal analyzer 180 is provided by the computing device 190 such that the functionalities of both components are integrated into a signal component.

The computing device 190 is configured to receive the sampled spectrum data of the modulated electromagnetic signal 140' and calculate an evaluation parameter $\Delta$. As described in detail below, the evaluation parameter $\Delta$ is indicative of the neurological status of the subject's brain 12. In an alternative embodiment, the evaluation parameter $\Delta$ is calculated by the signal analyzer 180 and is provided to the computing device 190. The computing device 190 may use the evaluation parameter $\Delta$ to provide a neurological status indicator to the operator of the neurological status evaluation apparatus. For example, the computing device 190 may compare the evaluation parameter $\Delta$ to one or more sample evaluation parameters $\Delta$ that are indicative of sufficient or insufficient blood flow to the subject's brain 12 to maintain neurological function. The evaluation parameter $\Delta$ may indicate the sufficiency or insufficiency of cerebral perfusion, ischemia, and/or infarction based on the changes in the dielectric properties of the brain that are caused by cerebral perfusion, or lack of cerebral perfusion, to the brain.

The computing device 190 may then output the neurological status indicator to the operator. The neurological status indicator may include, but is not limited to, graphics displayed on a graphical display device associated with the computing device 190 (e.g., a liquid crystal display screen), a text message displayed on the graphical display device associated with the computing device 190, numerical values displayed on the graphical display device, light emitting diodes associated with the computing device 190, auditory messages, and wireless transmission to an external computing device.

As stated above, the embodiments described herein may measure the changes in an electromagnetic signal induced by passage through the cranium of a human head to determine if a significant change in patient neurologic status has occurred. In one embodiment, a neurological status evaluation apparatus is operable to detect the sufficiency of resuscitation efforts during a cardiac crisis such as can occur as a result of CPR during cardiac arrest.

Electromagnetic fields interact with the charges and ions contained in biological tissue, such as the brain. At low frequencies (~MHz), such fields induce ionic motion and currents such that there is energy lost from the electromagnetic wave in doing the work to move these charges. As a result, the electromagnetic absorption and scattering of biological tissue at lower frequencies is very dependent upon the ionic solute quantity of the tissue. This electromagnetic absorption process is known as the beta ($\beta$) dispersion of electromagnetic fields.

At higher frequencies (~GHz), the ionic mobility becomes more limited in biological tissue and fluids. As a result, the $\beta$ dispersion of electromagnetic fields is reduced. Electromagnetic interactions in this frequency regime are dominated by the interaction of the electric dipoles of water molecules with the electromagnetic field. This absorbs energy from the fields as the water molecules absorb energy, a process called gamma ($\gamma$) dispersion. Overall, $\beta$ dispersion dominates for frequencies less than 1 GHz, while γ dispersion is more important for frequencies greater than 3 GHz.

Christ et al. recently introduced a model of the interaction of electromagnetic absorption in layered biological tissues (Christ A, Samaras T, Klingenbock A, and Kuster N., "Characterization of the electromagnetic near-field absorption in layered biological tissue in the frequency range from 30 MHz to 6,000 MHz." *Phys Med Biol* 51: 4951-4965, 2006). If an electromagnetic wave of wave vector k is propagating in the z-direction normal to the tissue plane, one can write the electric field components as:

$$E_i(k,z) = E_i^{incident} e^{ikz} E_i^{reflected} e^{-ikz-i\phi}, \quad \text{Eq. (1)}$$

where the components of E are transverse to k, and consist of incident and reflected components.

The peak average specific absorption rate (SAR), which is the power loss from the electromagnetic field in tissue per unit volume, can then be estimated as:

$$SAR(k, m) \approx \frac{A}{2m} \int_0^l dz \sigma |E_{PEAK}(k, z)|^2, \quad \text{Eq. (2)}$$

where the electromagnetic wave is incident normally on the tissue, the tissue has mass m over area A with thickness l, and conductivity σ. In addition, $E_{PEAK}$ is the maximum amplitude of E over the tissue thickness l. It should be noted that σ depends on the frequency of the electromagnetic wave, as discussed above. Also, changes in the permittivity ε within the tissue can result in some of the incident electromagnetic energy being reflected from the various interfaces. In addition, it is implicitly assumed in Eq. (2) that the electric field E penetrates the entire tissue volume; thus Eq. (2) neglects "shielding" effects.

This approach can be generalized to tissues with conductivity and permittivity varying in the z-direction. Again, assuming that the electromagnetic wave is incident normally on the tissue, and allowing the conductivity σ and permittivity ε to vary as a function of z, one can write an approximate expression for the magnitude of the electric field E(z) as:

$$E(z) \approx E_o e^{-\kappa(z)z}, \quad \text{Eq. (3)}$$

where $E_o$ is the incident amplitude of the electric field, and κ can be written as:

$$\kappa \equiv \omega \sqrt{\frac{\varepsilon \mu}{2}} \left\{ \sqrt{\left(\frac{\sigma}{\varepsilon \omega}\right)^2 + 1} - 1 \right\}^{1/2}, \quad \text{Eq. (4)}$$

where μ and ε are the permeability and permittivity of the tissue respectively, and ω is the angular frequency of the electromagnetic signal. Note that both ε and μ are implied functions of z as well. Generalizing Eq. (2) yields:

$$SAR \approx \frac{A}{2m} |E_o|^2 \int_0^l dz \sigma(z) e^{-2\kappa(z)z}, \quad \text{Eq. (5)}$$

where l is the total tissue width along the z-direct, as above.

It is interesting to take the limit for SAR of small σ. This yields the expression:

$$SAR \approx \frac{A}{2m} |E_o|^2 \int_0^l dz \sigma(z) e^{-\sigma(z)(\mu/\varepsilon)^{1.2} z}. \quad \text{Eq. (6)}$$

This is the frequency-independent limit for κ, and is a reasonable approximation in poor conductors. Note that to leading order in σ, the SAR is linear in σ and therefore to small changes in this parameter. Also note that small changes in ε(z) can substantially change the SAR either increasing or decreasing the magnitude of this parameter.

It would be useful to relate Eq. (6) to a measurable parameter that can be obtained in a real system. In a given antenna, an incident electric field induces a time varying voltage at the antenna terminals, as expressed by:

$$V = \alpha E \quad \text{Eq. (7a)}$$

where V is the output voltage of the antenna, E is the magnitude of the incident electric field, and α is a constant which depends on the detailed electrical parameters of the antenna. If one postulates an array of antenna such that one can denote the quantity $V_{ij}$ as the voltage at antenna j when antenna i is transmitting, one can define an evaluation parameter Δ(t) such that $$\Delta(t) = F[V_{12}(t), V_{13}(t), \ldots, V_{ij}(t)] \quad \text{Eq. (7b)}$$

where F is a functional of the time-varying voltages for the antenna pairs (i,j).

Note that the above equations and description are only an approximate model, as it is assumed that: (1) the incident electromagnetic signal is a plane wave, and (2) these expressions implicitly assume "far field" electromagnetic behavior. Assumption 2 holds for distances less than (λ/2π), where λ is the wavelength of the electromagnetic signal. The near field dimension ranges from 2.5 to 12.5 cm for frequencies of 1.2 to 0.4 GHz respectively. Being in the near field regime results in the evaluation parameter being more sensitive to cerebral perfusion, neurologic function such as brain activity, or both cerebral perfusion and neurologic function, and may actually increase overall changes in the evaluation parameter Δ for small changes in cerebral perfusion, neurologic function, or both cerebral perfusion and neurologic function.

Figure 2:
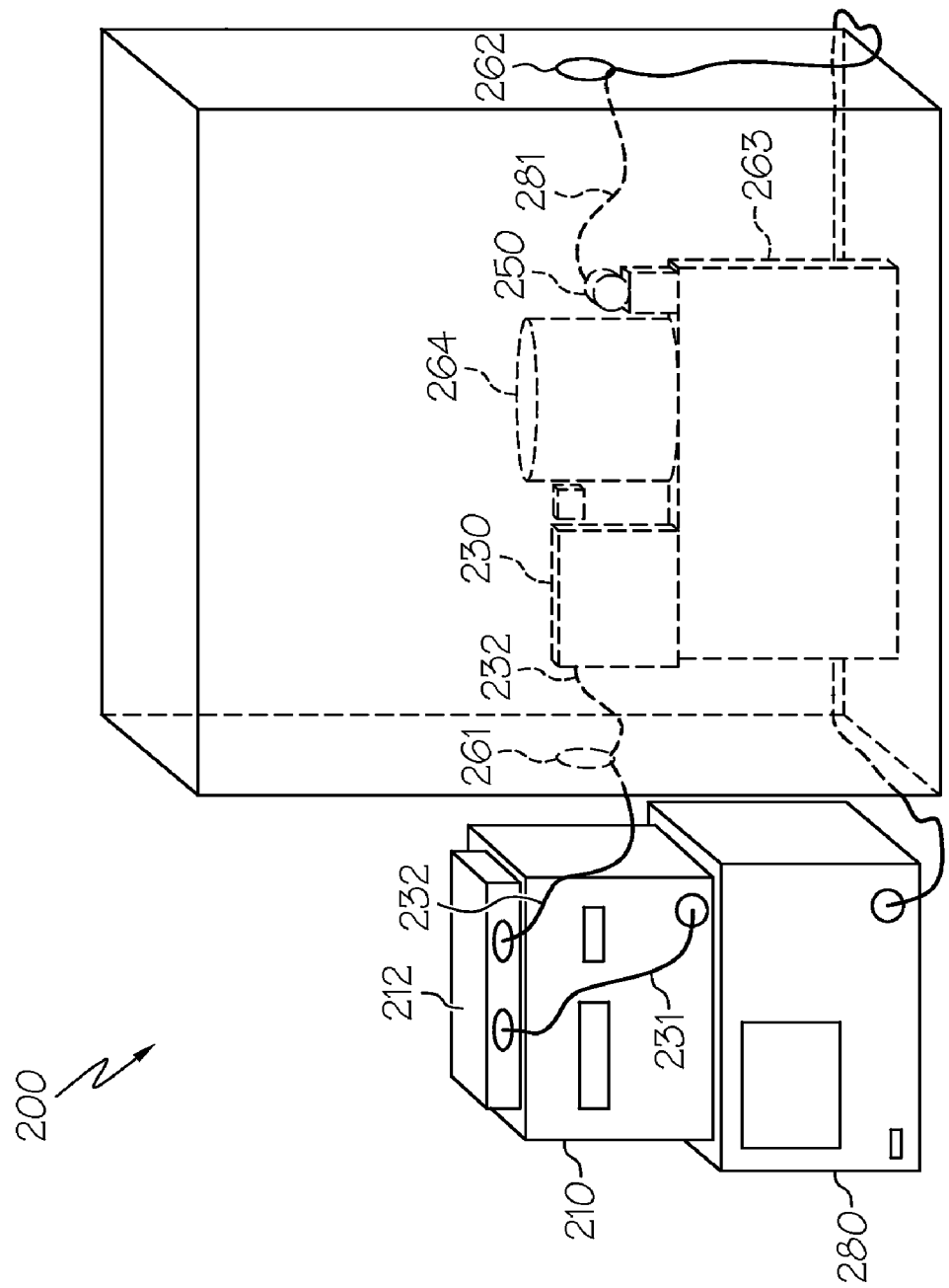
FIG. 2 depicts a schematic illustration of a neurological evaluation apparatus according to one or more embodiments shown and described herein.

Referring now to FIG. 2, a prototype neurological status evaluation apparatus 200 was constructed in accordance with the schematic of FIG. 1. It should be understood that embodiments are not limited to the components and configurations depicted in FIG. 2. A signal generator 210 was used to generate the electromagnetic signal. The signal generator 210 was electrically coupled to a radiofrequency amplifier 212 by electrical conductors 231. The transmitting antenna 230 was configured as a circular patch antenna with an operating frequency of 931 MHz, and the receiving antenna 250 was configured in this fashion as well. The output of the radiofrequency amplifier 212 was coupled to the transmitting antenna 230 via an electrical conductor 232. The receiving antenna 250 was coupled to a signal analyzer (HP 8560E by Hewlett-Packard of Palo Alto, Calif. via an electrical conductor 281.

Figure 3B:
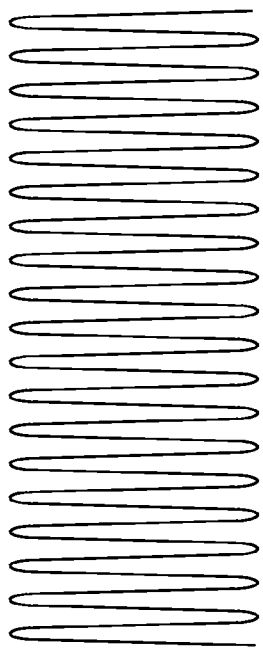
FIG. 3B schematically depicts an exemplary modulated electromagnetic signal according to one or more embodiments shown and described herein.
Figure 3A:
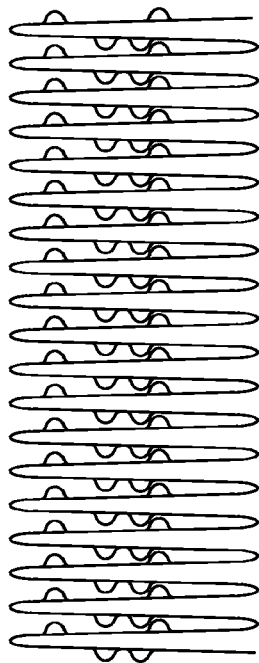
FIG. 3A schematically depicts an exemplary electromagnetic signal according to one or more embodiments shown and described herein.

Referring now to FIG. 3A, an exemplary wave form of an electromagnetic signal transmitted by the transmitting antenna 130 is schematically shown. As described above, the exemplary electromagnetic signal crosses the patient's brain and is received as a modulated electromagnetic signal at the receiving antenna 150. An exemplary wave form of a modulated electromagnetic signal is schematically shown in FIG. 3B. It is noted that FIG. 3B is only a schematic representation of the modulated electromagnetic signal and does not illustrate changes such as amplitude modulation, for example. The waveform has changed due to noise and absorbance and scattering characteristics of the brain, blood flow in the brain, and neurological activity in the brain such as decreased brain activity resulting from insufficient blood flow and the like.

Figure 3C:
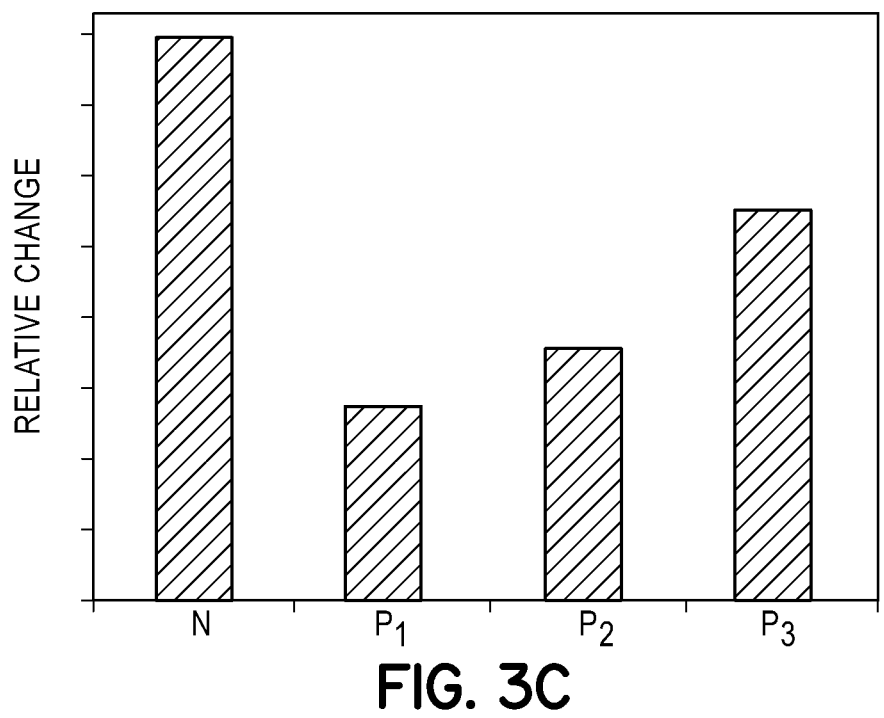
FIG. 3C depicts a graph illustrating an exemplary relative evaluation parameter responses of the modulated electromagnetic signal according to one or more embodiments shown and described herein.

In some embodiments, the modulated electromagnetic signal is transformed (e.g., by a Fourier transformation), to extract spectrum data. Multiple frequency sweeps may be transformed to produce a transformation of the modulated electromagnetic signal. FIG. 3C graphically illustrates exemplary relative change in the evaluation parameter for total normal brain (N), and three patient conditions in which blood flow to the brain is compromised such as during a cardiac crisis like cardiac arrest ($P_1$), when blood flow is inadequately restored ($P_2$), and when blood is adequately restored ($P_3$) to improve neurological outcome upon ROSC. As shown in FIG. 3C, the effect of compromised blood flow to the brain, such as occurs during a cardiac crisis like cardiac arrest, as well as the level of blood flow that occurs during resuscitation produces different evaluation parameter responses such that resuscitation efforts that adequately maintain blood flow may be differentiated from inadequate resuscitation efforts.

Figure 4A:
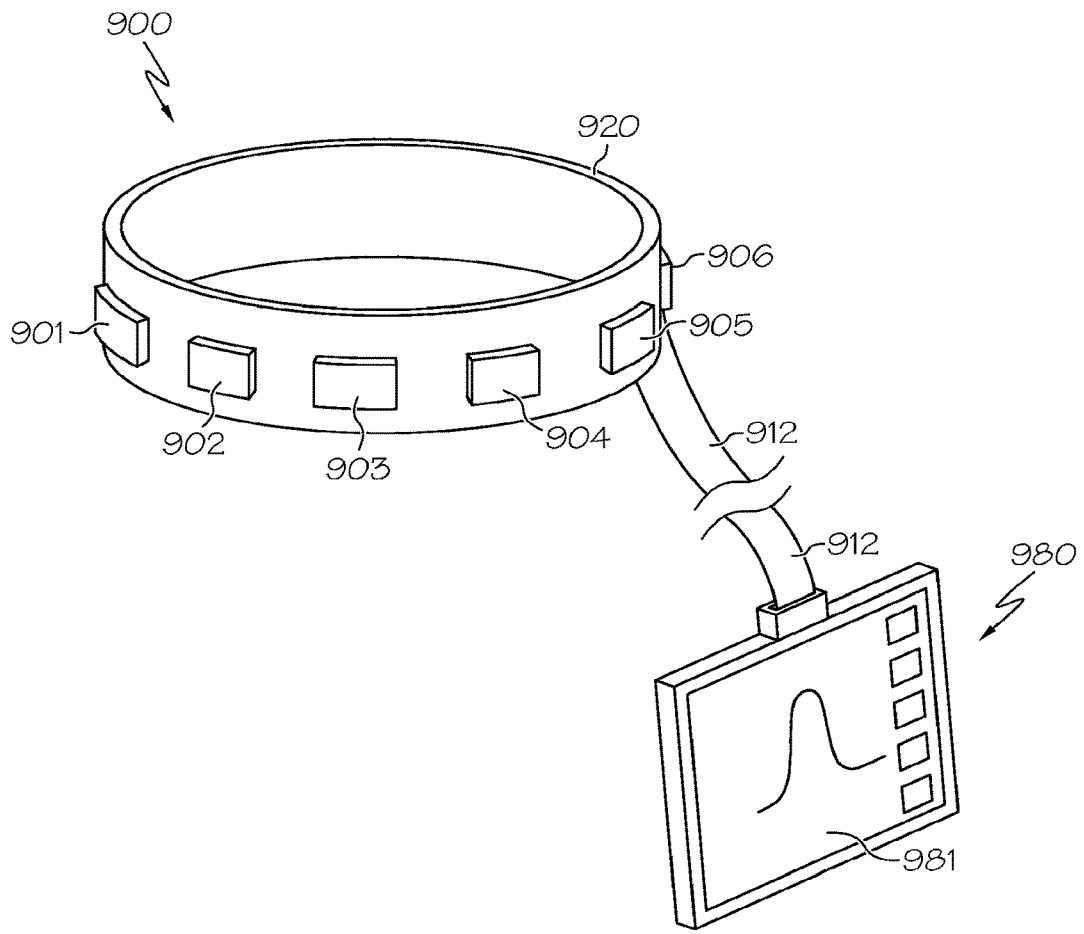
FIG. 4A schematically depicts an exemplary transcranial neurological evaluation apparatus according to one or more embodiments shown and described herein.

Referring now to FIG. 4A, a portable transcranial neurological evaluation apparatus 900 is illustrated. The transcranial neurological evaluation apparatus 900 generally comprises a plurality of transceiver devices 901-912 positioned around a circumference of a headband portion 920 that is configured to be positioned onto the head of a portion without the transceiver devices 901-912 physically contacting the patient's head. The transcranial neurological evaluation apparatus 900 is a non-invasive, trans-cranial, transdermal sensor that is operable to detect blood flow, neurological activity, or both blood flow and neurological activity in the patient's brain.

The headband portion 920 may be configured as a fabric, gauze, or other flexible material that is not electrically conductive. Each transceiver device 901-912 comprises a transmitting antenna and a receiving antenna such that it may both transmit and receive electromagnetic signals. The transmitting antenna may transmit the electromagnetic signal, and the receiving antenna may receive the modulated electromagnetic signal after propagating through the patient's cranium, as described above. Each transceiver device is paired with another transceiver device located at a different section of the headband portion 920.

Figure 4B:
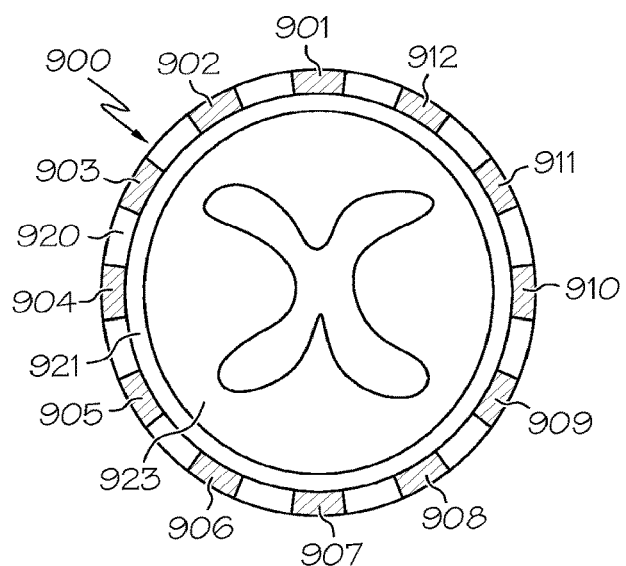
FIG. 4B schematically depicts an exemplary transcranial neurological evaluation apparatus positioned on a human head according to one or more embodiments shown and described herein.

Any number of transceiver devices may be utilized. In order to achieve 95% coverage of the brain's volume for detecting blood flow, neurological activity, or both blood flow and neurological activity, multiple pairs of transmitting and receiving antennas may be used. In one embodiment, three pairs of transceiver devices are used. In another embodiment, the transcranial neurological evaluation apparatus 900 comprises a first row of transceiver devices in a first horizontal plane, and a second row of transceiver devices in a second horizontal plane (e.g., one row of eight transceiver devices on top of another row of transceiver devices around the circumference of the headband portion 920). Twelve transceiver devices are depicted in FIGS. 4A and 4B for ease of illustration.

A combination of a de-multiplexer (de-mux) and multiplexer (mux) can be used to accomplish the creation of an array (in pairs) of the antennas of the transceiver devices. A de-mux may connect a single transceiver to any of the user selected transmitting antennas. The receiving antennas may be connected to a mux which may have a single output to a signal analyzer. In one embodiment, the signal analyzer (not shown in FIG. 4A) is a separate, handheld component (e.g., a handheld computing device 980) operated by the user of the transcranial neurological evaluation apparatus 900. In another embodiment, the signal analyzer is incorporated into the headband portion 920).

In some embodiments, a smart sensor system may be provided that can detect head thickness as well as correct for poor placement, skull shape or movement of the headband while covering 95% of the brain's volume. A smart sensor algorithm may detect the transceivers that are aligned and working properly and thereby focus on those transceivers for diagnostic and monitoring. Thus, if transcranial neurological evaluation apparatus 900 is deployed with an array of four pairs of transmitters and receiving antennas, the smart sensor system can use all four if capable, or only the pairs that respond according to set thresholds. Accordingly, the smart sensor system can correct for poor placement, skull shape or movement of the headband.

A microprocessor (e.g., a microprocessor included in the handheld computing device 980) may digitally select the correct corresponding pair of antennas, collect necessary data from the signal analyzer, and repeat the process until data from all pairs have been collected. In the embodiment depicted in FIG. 4A, the transceiver devices 901-912 are electrically coupled to a computing device 980 by a wired connection 912. Signal amplitude for each antenna pair and configuration data (e.g., a size of the patient's head) may be stored.

In some embodiments, data from the transceiver devices 901-912 may be provided to the computing device 980 wirelessly. Power to the transceiver devices 901-912 may be provided by the wired connection 912, or by a power supply located on the headband portion 920.

The computing device 980 includes a processor may take on a variety of configurations, such as a general-purpose computer, a specific purpose computer, a laptop computer, a tablet computer, a smart phone, and the like. As stated above, the functionality of the signal analyzer and the computing device 980 may be performed entirely by the computing device 980. The computing device 980 may be capable of conveying neurological status indicator on a graphical user interface 981. Data, including, but not limited to, the neurological status indicator, may also be transmitted to one or more remote computing devices.

Referring now to FIG. 4B, a top view of a transcranial neurological evaluation apparatus 900 applied to a human head comprising a skin and skull layer 921 and a brain 923 is illustrated. Each transceiver device 901-912 has a paired transceiver device associated therewith. For example, transceiver device 904 is paired with transceiver device 910. In one embodiment, the transmitting antenna of each transceiver device 901-912 of the plurality of transceiver devices is activated sequentially to transmit the electromagnetic signal through the skin and skull layer 921 and brain to be received by the receiving antenna of the remaining transceiver devices. As an example, and not a limitation, the transmitting antenna of transceiver device 904 may transmit an electromagnetic signal as described above, which is then received by the receiving antenna of transceiver devices 907-912.

When the electromagnetic radiation of the electromagnetic signal is incident on the biological tissue, part of it will be reflected back, and part of it will be transmitted and/or scattered into or away from the medium. For electromagnetic radiation passing deep inside the brain, the electrical field will interact with multiple media at multiple boundaries. A simplified model is shown below:

The transcranial neurological evaluation apparatus 900 should account for the air-skin interface without the use of gels or conduction media because it is to be field deployable. The transcranial neurological evaluation apparatus 900 may account for this interface in part by detecting the total volume and circumference of the head. At each of these interfaces, the radiation is deflected by an angle $\alpha_2$, which then becomes the incident angle for the next layer. The incident wave would have undergone reflection and transmission at each of the boundaries and absorption in each of the media, the extent of which is determined by the dielectric properties of each of the media.

The fate of the radiation would be different when passing through a subdural or epidural hematoma, modeled as a thin film of blood between the brain tissue and skull.

The array of transceiver device 901-912 can be used to measure the properties of an electromagnetic signal transmitted across the brain 923. The resultant signal output may be the result of wave energy absorption, reflection and scattering resulting from the changing dielectric properties of the different media. Different levels of blood flow, neurological activity, or both blood flow and neurological activity may impact the incident radiation to different extents depending on the detailed geometry of these parameters. The transceiver devices 901-912 will receive the modulated electromagnetic signal from a given transceiver device after traversing the brain. The highest signal intensity will typically be in the direction of the corresponding transceiver device 901-912. In a patient having a cardiac crisis, the path and medium of the radiation will change due to the blood flow in the brain and alterations in the electromagnetic properties of that tissue. As a result, in an array of transceiver devices 901-912 surrounding the surface of a head, the receiving antenna of the transceiver device that picks up the highest intensity with respect to the transmitting antenna will also change.

Embodiments may be operable to alert field and/or medical personnel if a patient starts having a cardiac crisis that compromises blood flow to the brain or if resuscitation efforts for a patient experiencing a cardiac crisis is insufficient. It could be deployed on one patient for diagnostics as a set-it-and-forget-it monitor. Lightweight and taking seconds to deploy, the headband array and wireless or wired handheld device can be used as a triage tag with color coding, alarm and text messaging to notify medical personnel of the patient's status. Embodiments may provide an easy to read screen with quantitative and qualitative diagnostic information concerning the sufficiency of blood flow to the brain during and after a cardiac crisis and during resuscitation efforts. Embodiments may also be configured to have an automatic call or response option to rapidly establish communication with hospital, helicopter or ambulance teams.

Example

Data were obtained on the effect of whole-brain ischemia following cardiac arrest in a porcine ICH model on the electromagnetic signal as it propagates through the pigs' head. Data were collected for 5 measurements prior to injection of euthasol, which is a euthanasia solution that induces cardiac arrest. After inducing cardiac arrest, 10 additional measurements were obtained over a span of 10 minutes. For these measurements, data were collected with antennae pairs that were centrally located on the head.

Figure 5:
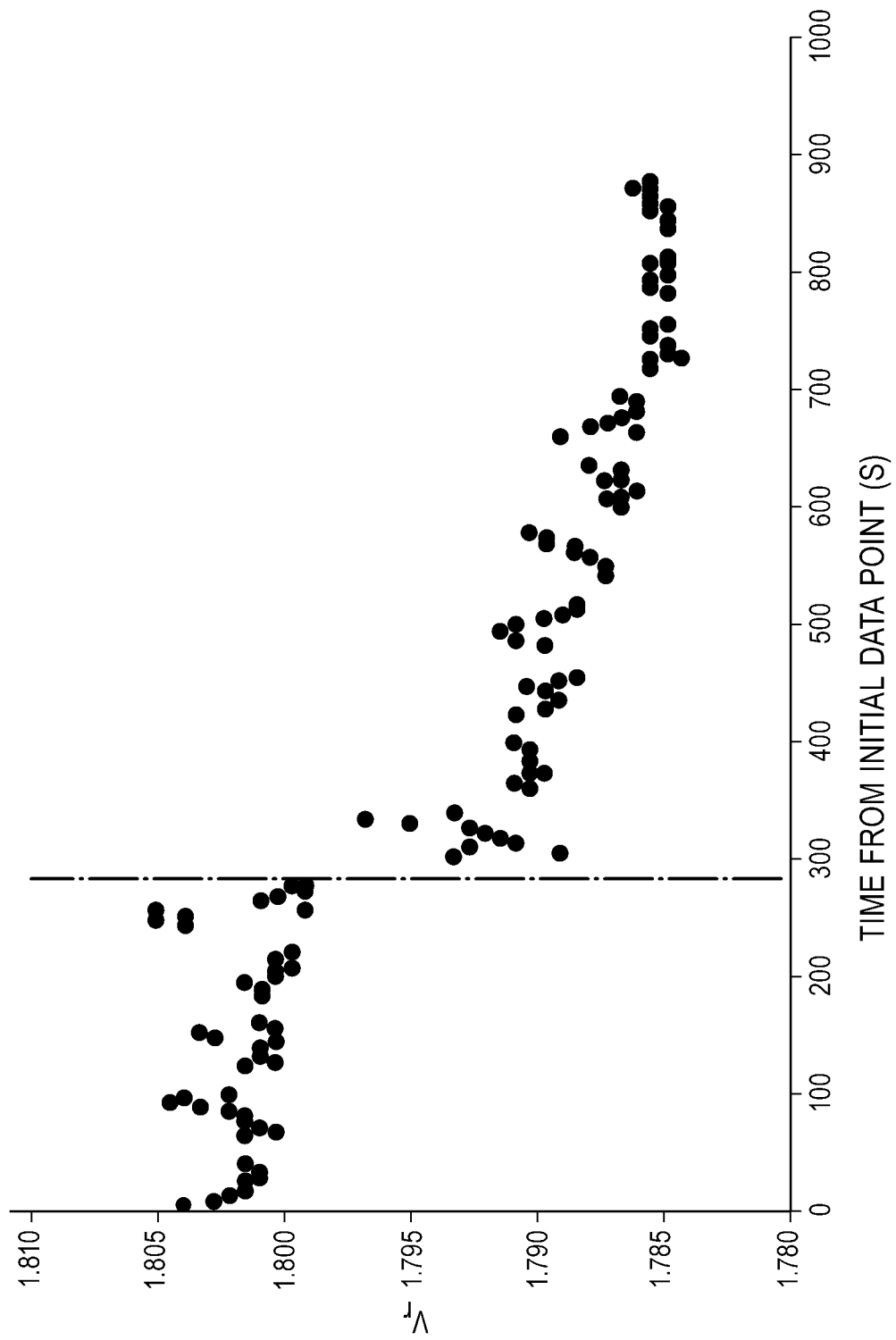
FIG. 5 is a graph of signal data from a frontal/sagittal antenna pair prior to and after pig sacrifice.

The measured signal for the 5 measurements collected prior to euthasol injection (control) was averaged and standard deviation was calculated. Each of the next 10 measurements were then compared to this average. Following porcine sacrifice and cessation of cardiac activity (vertical line on FIG. 5), the measured signal exhibits a rapid decrease followed by a slow, steady decrease before leveling off. The rapid change is most likely due to cessation of blood flow to the brain, and the slow steady decrease most likely represents global ischemia and cell death.

Looking only at data collected from the central pair of antennae, for 60% of the pigs, a significant change was observed within 1 minute of injection of euthasol ($p<0.05$), and for 75%, a significant change was observed at 10 minutes post injection ($p<0.05$). When an array of 8 different pairs of antennae were considered together, a significant change between the control measurement and the first measurement after euthasol injection was found for at least 3 of the 8 pairs for all pigs (n=20) in the experiment.

For all of the pigs, as time increased after euthasol injection, signal variability (standard deviation) decreased. For all pigs, the standard deviation of the final signal measurement was always small than the standard deviation of control measurements. This observation may indicate that there is a time window for cell death that can be detected by looking at variation or other signal characteristic in the measured signal.

The data demonstrate the blood flow to the brain can be detected by measuring the electromagnetic signal as it propagates through the head. Moreover, the sufficiency of blood flow to the brain during a resuscitation effort, such as CPR, may also be detected based on changes in the electromagnetic signal. Further, cell death or ischemia during insufficient perfusion of the brain may also be detected.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A neurologic status evaluation system for use in detecting cerebral perfusion in a subject's head during a cardiac crisis, comprising:
   a signal generator configured to generate an electromagnetic signal at one or more frequencies;
   a transmitting antenna configured to transmit the electromagnetic signal;
   a receiving antenna positioned relative to the transmitting antenna such that an evaluation space is defined between the transmitting antenna and the receiving antenna, wherein the evaluation space is configured to receive the subject's head; and
   a computing device configured to:
      analyze a modulated electromagnetic signal V(t) generated by the receiving antenna after the transmitted electromagnetic signal has propagated through the head,
      calculate, based on the modulated electromagnetic signal V(t), an evaluation parameter Δ(t) indicative of electromagnetic absorption, modulation and scattering in the head, wherein:

$$\Delta(t)=F[V(t)],$$

F is a function whose value is dependent on the parameters in brackets, and

V(t) is a voltage at time t measured at the receiving antenna when the transmitting antenna is transmitting, and generate a neurologic status indicator of a head under evaluation based on the evaluation parameter Δ(t).

2. The neurologic status evaluation system of claim 1, wherein the computing device is further configured to:

calculate the evaluation parameter Δ(t) based on the electrical properties included in the head, wherein the modulated electromagnetic signal is altered based on the electrical properties included in the brain based on the sufficiency of resuscitation efforts on the patient.

3. The neurologic status evaluation system of claim 2, wherein the computing device is further configured to:

calculate the evaluation parameter Δ(t) based on the conductivity and dielectric constant of the biological tissue under evaluation, wherein the modulated electromagnetic signal as compared to the transmitted electromagnetic signal is altered based on the conductivity and dielectric constant of the brain.

4. The neurologic status evaluation system of claim 1, wherein the evaluation parameter Δ(t) is calculated by:

$$\Delta(t)=F[V_{12}(t),V_{13}(t),\ldots,V_{ij}(t)]$$

the transmitting antenna and the receiving antenna are part of an array of antennae including a plurality of transmitting and receiving antenna pairs each including a transmitting antenna i and a receiving antenna j, $V_{ij}(t)$ is the voltage at time t measured at the receiving antenna j when the transmitting antenna i is transmitting.

5. The neurological status evaluation apparatus of claim 1, wherein the biological tissue under evaluation that is included in the evaluation space is not in contact with the transmitting antenna or the receiving antenna.

6. A method of detecting the sufficiency of a resuscitation effort of a patient experiencing a cardiac crisis utilizing the apparatus of claim 1.

7. The method of claim 6, wherein the cardiac crisis is cardiac arrest.

8. The method of claim 6, wherein the resuscitation effort is cardiopulmonary resuscitation.

9. A method of predicting the outcome of a patient experiencing a cardiac crisis utilizing the apparatus of claim 1.

10. The method of claim 9, wherein the cardiac crisis is cardiac arrest.

11. The method of claim 9, wherein the resuscitation effort is cardiopulmonary resuscitation.

* * * * *